United States Patent [19]

Delts

[11] Patent Number: 5,258,182
[45] Date of Patent: Nov. 2, 1993

[54] INSECT REPELLENT METHOD

[76] Inventor: Glenwood Delts, 920 Stephens St., Greensboro, N.C. 27406

[21] Appl. No.: 911,750

[22] Filed: Jul. 10, 1992

[51] Int. Cl.$^5$ ............................................. A01N 65/00
[52] U.S. Cl. .................................................. 424/195.1
[58] Field of Search ...................................... 424/195.1

[56] References Cited
PUBLICATIONS

Abbott et al.; Cancer Research, Supplement, Part 2, vol. 26, No. 4, Apr. 1966; pp. 391–393 and 495.

*Primary Examiner*—Jerome D. Goldberg

[57] ABSTRACT

An insect repellent can be conveniently prepared from the leaves and branches of *Myrica cerifera* plant by boiling the same in water. The solution can then be used to dip household pets such as dogs or cats therein to provide a durable insect barrier and repellent for the animals.

6 Claims, No Drawings

INSECT REPELLENT METHOD

BACKGROUND OF THE INVENTION

1. Field of the Invention

The invention herein pertains to insect repellents and particularly to insect repellents for dogs, cats and other pets that carry fleas.

2. Description of the Prior Art and Objectives of the Invention

Various insect repellents have been used for many years to kill and control fleas, ticks and other insects which are carried by various animals including household pets. Certain of the commercial insecticides and flea repellents can be dangerous and irritate the skin of an animal while other commercially available insect repellents and shampoos have proven to be relatively ineffective under certain adverse conditions. The present invention provides certain advantages over prior insecticides and known chemical repellents and therefore one objective of the present invention is to provide an insect repellent for use on dogs, cats and other household pets which is very effective in repelling fleas and which will not irritate the skin of the animal.

It is another objective of the present invention to provide an insect repellent which can be easily and inexpensively manufactured and used over a prolonged period without irritation to the skin of the animal.

It is yet another objective of the present invention to provide an insect repellent and method of preparing the same which will not be dangerous to the animal or to the user in its application.

Various other objectives and advantages of the present invention become apparent to those skilled in the art as a more detailed description is set forth below.

SUMMARY OF THE INVENTION

The insect repellent described herein is formed from the bark and leaves of a *Myrica cerifera* (Family Myricaceae), a decorative plant which is common throughout the south and other areas of the United States. The insect repellent is formed by clipping leaf bearing branches from the plant which is commonly referred to as a Wax-Myrtle and by placing the branches with leaves in boiling water for approximately two hours. The solution or tea thus formed is then cooled and thereafter dogs, cats or other pets can be dipped into the solution. The solution coats the fur or hair of the animals and after drying, repels fleas, ticks and other insects from entering the fur.

DETAILED DESCRIPTION OF THE PREFERRED EMBODIMENT

In the preferred form of the invention, approximately four to six ounces of small branches with leaves attached from a *Myrica cerifera* plant are freshly cut and are placed in a suitable container with one and one-half to two ($1\frac{1}{2}$-2) gallons of ambient temperature water. Heat is applied and the water is raised to boiling temperature such as by heating the container on a stove or the like. Boiling is continued for approximately two hours until a uniform light brown solution is obtained. Heating is then terminated and the solution is allowed to cool to room temperature. Thereafter, all leaves, branches and extraneous debris are removed from the container and the solution may be strained through a clean cheesecloth to remove any miscellaneous particles of bark or the like remaining therein. After cooling the original container or another can be used for dipping small pets such as dogs or cats therein whereby the fur of the animal is saturated with the solution. Thereafter, the pet is dried such as with a towel or an electrical blow dryer and the animal is then insect repellent. It is found that by treating pets in the early spring and late summer that insects are sufficiently controlled and repelled throughout the year.

Various methods of applying the solution to the animals can be used such as spraying or brushing the solution onto the animals fur. However, dipping has been found to be easy and convenient and for this reason is the preferred method of application. Perfumes or other additives may be added to the cooled solution to enhance its sales appeal.

The examples and descriptions provided herein are for explanatory purposes and are not intended to limit the scope of the appended claims.

I claim:

1. A method of repelling insects from the coat of an animal comprising the steps of: applying an insect repelling amount of a *Myrica cerifera* solution to the coat of the animal and allowing the applied solution to repel insects.

2. The method of claim 1 and including the step of drying the solution after application.

3. The method of claim 1 wherein the step of applying the solution to the animal comprises the step of dipping the animal in the aqueous solution to saturate the animal's hair.

4. A method of repelling insects from the outer hair of an animal comprising treating the outer hair of the animal with an effective insect repelling amount of a *Myrica cerifera* solution to repel insects therefrom.

5. The method of claim 4 wherein the step of treating the animal with a *Myrica cerifera* solution comprises brushing said *Myrica cerifera* solution onto the outer hair of the animal.

6. The method of claim 4 wherein the step of treating the animal with a *Myrica cerifera* solution comprises dipping the animal into said *Myrica cerifera* solution.

* * * * *